United States Patent [19]

Ciffolillo

[11] 3,990,112
[45] Nov. 9, 1976

[54] PROTECTIVE GARMENT
[75] Inventor: Joseph Anthony Ciffolillo, North Easton, Mass.
[73] Assignee: Codman & Shurtleff, Inc., Randolph, Mass.
[22] Filed: May 2, 1975
[21] Appl. No.: 574,111

[52] U.S. Cl. .................................. 2/424; 2/205; 128/139; 2/422
[51] Int. Cl.² .................................................. A42B 1/04
[58] Field of Search .................. 2/202, 205, 2, 3 R, 2/14 B, 14 W, 14 C, 14 D, 206, DIG. 7; 128/139, 142.5, 142.4, 141

[56] References Cited
UNITED STATES PATENTS
1,560,997  11/1925  Kelly ............................. 2/DIG. 7
1,800,051  4/1931   Blanco ............................ 128/139 X
2,641,768  6/1953   Pipher ............................ 2/205
3,363,262  1/1968   Lindblom ......................... 2/14 D
3,529,594  9/1970   Charnley ......................... 128/139
3,908,196  9/1975   Ferraro .......................... 2/14 W Primary Examiner—Thomas F. Callaghan
Assistant Examiner—Peter Nerbun

[57] ABSTRACT

A protective garment for use with a body exhaust helmet has a hood adapted to cover the head of a wearer and the hood is provided with a fenestration in the vicinity of the eyes of the wearer. A transparent plastic sheet is secured around the periphery of the inside of the fenestration and tabs extend beyond the area of securement on opposed sides of the sheet to attach the hood to a portion of the body exhaust helmet.

3 Claims, 10 Drawing Figures

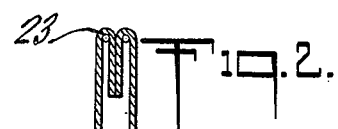
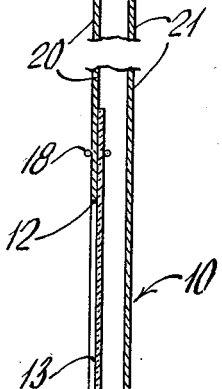
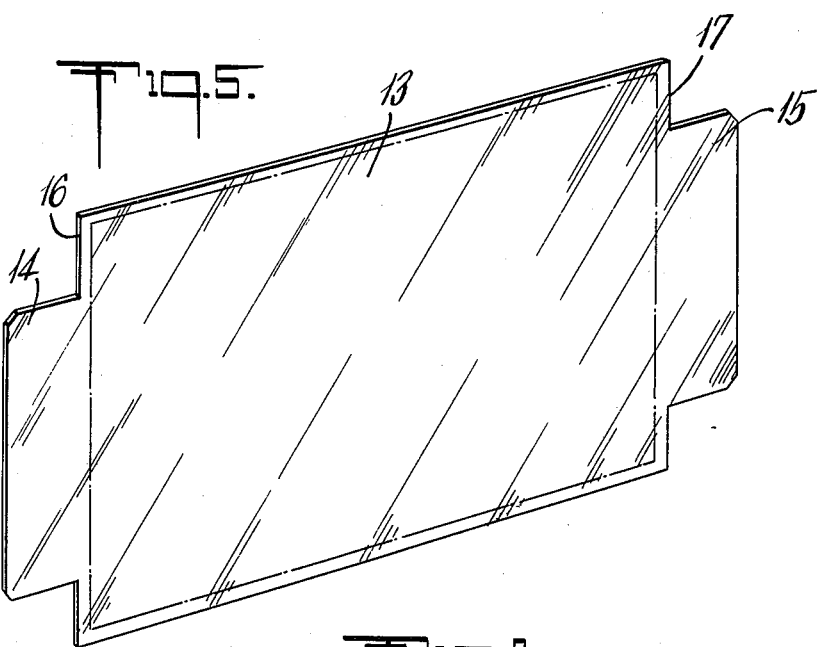
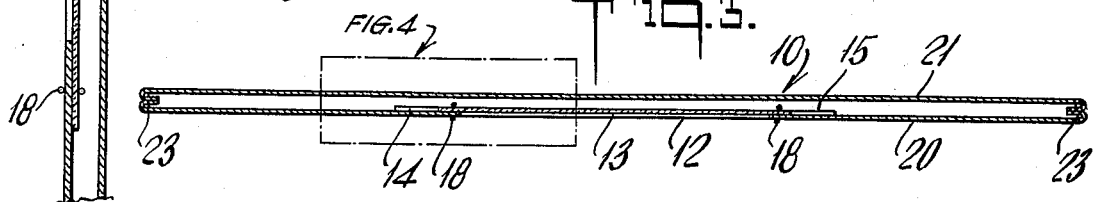
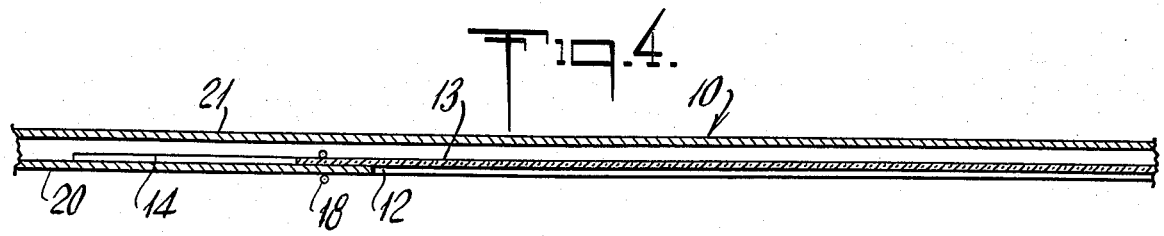

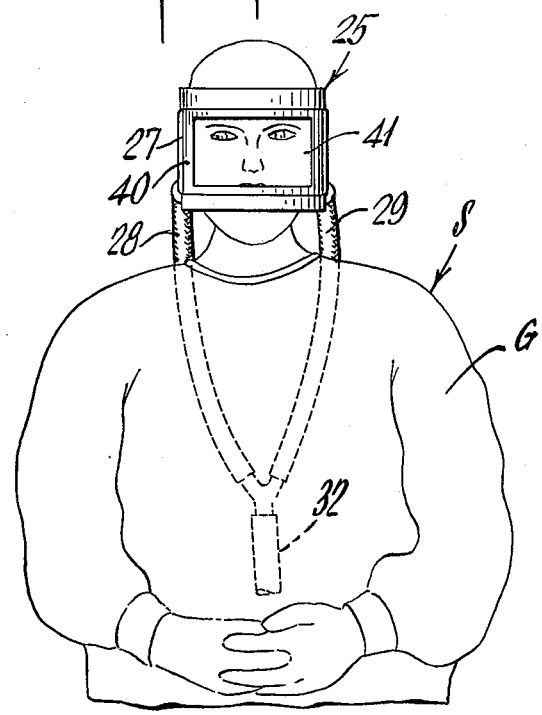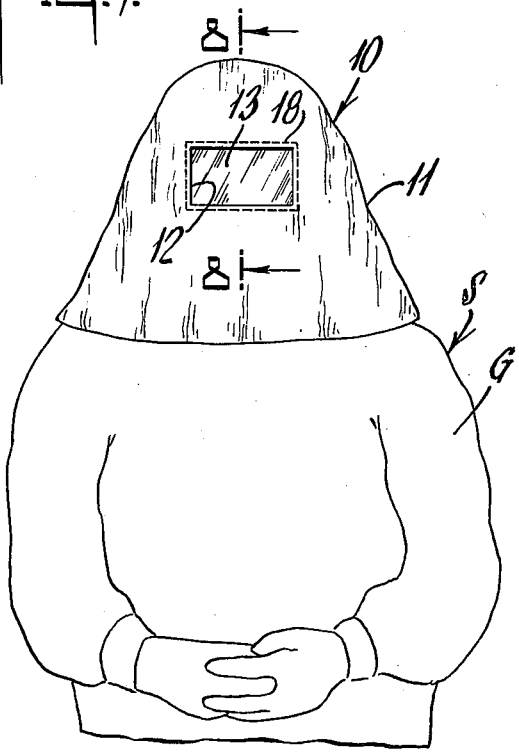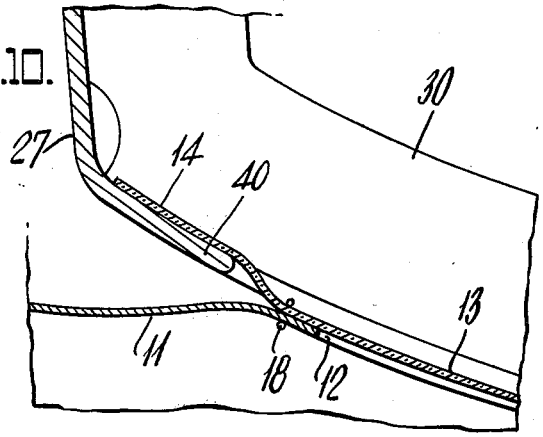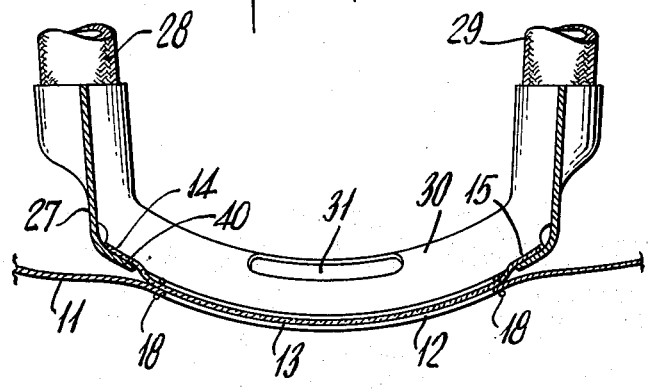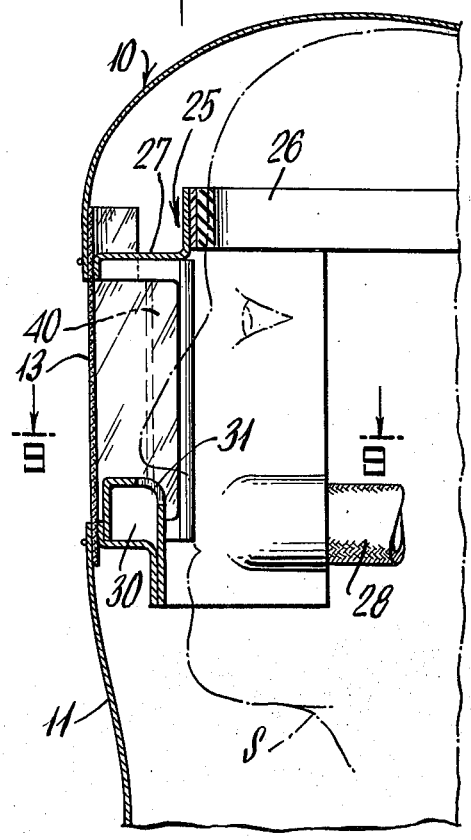

PROTECTIVE GARMENT

BACKGROUND OF THE INVENTION

This invention relates to protective garments and, more particularly, to a unique hood for use in combination with a body exhaust helmet utilized in a total body exhaust system.

The type of body exhaust system contemplated by the present invention is illustrated and described in U.S. Pat. No. 3,529,594. This type of system is intended for use during surgical procedures when it is necessary that any contaminants on the body or in the exhaled breath of a surgeon and his assistants be totally prevented from contacting the patient. In the system illustrated and described in the above-cited U.S. Patent, the body of the operator is entirely enclosed within a one-piece gown that is partially supported by an exhaust helmet worn on the head of the operator.

Heretofore, the helmet was provided with a glass or plastic shield which was secured directly to a frame extending outwardly from the helmet. The gown utilized with this type of helmet was equipped with a fenestration which was secured around its periphery directly over the outwardly extending frame. Although this system is very effective for preventing contaminants from leaving the body of the operator, the area of attachment of the gown fenestration to the helmet frame was not completely impenetrable by dust and other particles and, therefore, there remained a danger that such particles could be communicated to the wound of the patient.

SUMMARY OF THE INVENTION

In view of the foregoing, it is the main object of this invention to provide an improved protective garment in the form of a uniquely designed hood for use with a total body exhaust system and particularly for use in combination with an exhaust helmet.

The present invention contemplates the elimination of the glass or plastic shield in the outwardly extending flange on the exhaust helmet and the use of an extremely lightweight hood having a fenestration with a very lightweight transparent plastic sheet secured around the fenestration and having outwardly extending tabs on opposed sides of the sheet for coacting with the outwardly extending frame on the exhaust helmet.

This unique helmet structure provides an extremely lightweight component that virtually eliminates the possibility of airborne particles escaping from the head and shoulders of the operator. Also, the new hood of the present invention can be used in combination with a conventional surgical gown and may be donned and doffed much more readily than the complete gown and hood system presently being utilized.

BRIEF DESCRIPTION OF THE DRAWINGS

The foregoing objects and many of the attendant advantages of the invention will become more readily appreciated as the same becomes better understood by reference to the following detailed description when taken in conjunction with the accompanying drawings wherein:

FIG. 1 is a perspective view illustrating the unique hood of the present invention.

FIG. 2 is a sectional view taken along line 2—2 in FIG. 1.

FIG. 3 is a sectional view taken along line 3—3 in FIG. 1.

FIG. 4 is an enlarged view showing the portion in the boxed section in FIG. 3.

FIG. 5 is a perspective view of the plastic sheet utilized with the hood of FIG. 1.

FIG. 6 is a view of an operator wearing a surgical gown and an exhaust helmet.

FIG. 7 is a view similar to FIG. 6 illustrating the operator wearing the hood illustrated in FIG. 1.

FIG. 8 is a sectional view taken along line 8—8 in FIG. 7.

FIG. 9 is a sectional view taken along line 9—9 in FIG. 8.

FIG. 10 is an enlarged view of a portion of FIG. 9.

DESCRIPTION OF THE PREFERRED EMBODIMENT

The detailed description of a total body exhaust system described in U.S. Pat. No. 3,529,594 is incorporated herein by reference.

Referring to FIG. 1, the unique protective garment of the subject invention is shown generally at 10. Garment 10 comprises a flexible hood 11 that is designed to cover at least the head and shoulders of a surgeon, or other operator. Hood 11 has a rectangular fenestration 12 formed therein in the general vicinity of the eyes of the operator. A sheet 13 of transparent plastic material is secured around the inner peripheral edge of fenestration 12 and two integral tabs 14 and 15 extend outwardly from two opposed sides 16 and 17, respectively, of sheet 13. Sheet 13 is preferably formed from a thin flexible transparent plastic material and is preferably sewn along line 18 to the flexible reinforced paper material which forms the main body of hood 11. Although hood 11 may be formed from a single piece of flexible material, it is preferably formed by joining two symmetrical sheets 20 and 21 along a line 23, as by sewing or securing by other suitable means (see FIGS. 2 and 3).

Referring now to FIGS. 6 and 8, the exhaust helmet and other body exhaust equipment with which the hood of the present invention may be used will now be described in detail. The exhaust helmet shown generally at 25 comprises a head band 26 for securing the helmet to the head of a surgeon, or other operator, S. Secured to head band 26 and extending downwardly therefrom is a generally rectangularly-shaped open frame 27. Frame 27 has a pair of air exhaust tubes 28 and 29 secured thereto and extending rearwardly therefrom. Tubes 28 and 29 communicate with a channel 30 which extends across lower portion of the front of the frame and connects the forward ends of tubes 28 and 29. A crescent-shaped opening 31 extends through the inner surface of channel 30 and provides a passageway for withdrawing the exhaled breath from the operator. As will be seen from FIG. 8, opening 31 is positioned directly adjacent the nose and mouth of the operator.

Referring to FIG. 6, tubes 28 and 29 are connected to one end of a common tube 32 which, in turn, is connected at its other end to a vacuum source (not shown).

The procedure for donning the unique hood onto the exhaust helmet hood will be apparent from the foregoing description. As shown in FIG. 6, surgeon S may first don a conventional surgical gown G in the usual manner. Exhaust helmet 25 is then placed onto the surgeon's head and adjusted accordingly. The only additional step in the donning of this unique protective garment, is to place hood 11 over the head and shoulders of surgeon S and "snap" tabs 14 and 15 behind the inwardly extending flanges 40 and 41, respectively, extending inwardly on frame 27. The coaction between tab 14 and flange 40 is illustrated in detail in FIG. 10, wherein tab 14 is shown in a position inside of flange 40 and the remainder of hood 11 is shown in a position outside of the flange. This arrangement insures that sheet 13 will at all times remain in alignment with the opening formed between flanges 40 and 41 on frame 27. This, of course, is the area of vision of the operator and it must remain unimpaired at all times during the surgical procedure.

It will be apparent from the foregoing description that the present invention provides an extremely simplified approach for protecting an operative field from contamination by the operator. This is accomplished by modifying a previously existing exhaust helmet and providing a uniquely designed hood which is designed to coact with the modified exhaust helmet in a more efficient and effective manner. Because the hood is independent from the remainder of the protective garment, it can be made of a much lighter weight material and the connection between the hood and the exhaust helmet is virtually impenetrable by contaminants. The donning and doffing of the hood is greatly simplified and the alignment of the visual field of the hood with the visual field of the exhaust helmet is accurate and easily accomplished.

What is claimed is:

1. A protective garment, comprising in combination: an exhaust helmet; means for supporting said helmet on the head of a wearer; means for withdrawing air from said helmet; an open frame extending outwardly from said helmet in the vicinity of the eyes of a wearer; a flexible hood adapted to cover at least the head of a wearer; a fenestration in said hood in alignment with said open frame; a sheet of transparent material permanently secured around the periphery of said fenestration; and tab means on opposed sides of said sheet coacting with said frame to maintain alignment between said open frame and said sheet.

2. A protective garment for use in combination with an exhaust helmet having means for supporting said helmet on the head of a wearer and an open frame extending outwardly therefrom in the vicinity of the eyes of said wearer, comprising: a flexible hood adapted to cover said helmet and at least the head of said wearer; a transparent section in said hood permanently secured around its periphery thereto; and tab means on the inner surface of said hood on opposed sides of said section for releasably coacting with said open frame to maintain alignment between said frame and said transparent section.

3. The protective garment of claim 2, wherein said hood has a fenestration therein and said transparent section is a sheet of plastic secured to the inner surface of said hood around the periphery of said fenestration, said tab means being formed by extensions of said plastic beyond the area of securement.

* * * * *